United States Patent [19]

Znaiden et al.

[11] Patent Number: 5,750,123
[45] Date of Patent: May 12, 1998

[54] VITAMIN C DELIVERY SYSTEM

[75] Inventors: Alexander Paul Znaiden, Trumbull; Brian Andrew Crotty, Branford; Anthony Johnson, Fairfield, all of Conn.

[73] Assignee: Chesebrough-Pond's Co., Division of Conopco, Inc., Greenwich, Conn.

[21] Appl. No.: 696,422

[22] Filed: Aug. 13, 1996

Related U.S. Application Data

[60] Provisional application No. 60/022,509, Jun. 28, 1996.

[51] Int. Cl.$^6$ .................................................. A61K 7/48
[52] U.S. Cl. ........................... 424/401; 514/474; 514/844
[58] Field of Search ........................... 424/401; 514/474, 514/844

[56] References Cited

U.S. PATENT DOCUMENTS

| | | |
|---|---|---|
| 4,228,162 | 10/1980 | Luzzi et al. |
| 4,372,874 | 2/1983 | Modrovich ........................ 436/176 |
| 4,818,521 | 4/1989 | Tamabuchi . |
| 4,869,897 | 9/1989 | Chatterjee et al. ................ 424/47 |
| 4,923,900 | 5/1990 | De Villez . |
| 4,983,382 | 1/1991 | Wilmott et al. . |
| 5,078,989 | 1/1992 | Ando et al. ....................... 424/62 |
| 5,137,723 | 8/1992 | Yamamoto et al. ............... 424/400 |
| 5,140,043 | 8/1992 | Darr et al. ........................ 514/474 |
| 5,462,963 | 10/1995 | Bush et al. ........................ 514/248 |

FOREIGN PATENT DOCUMENTS

| | | |
|---|---|---|
| 44-22312 | 9/1969 | Japan . |
| 90/12752 | 11/1990 | WIPO . |

OTHER PUBLICATIONS

Chemical Abstracts vol. 105, No. 20, Nov. 17, 1986, Abstract No. 178434.

*Primary Examiner*—Jyothsan Venkat
*Attorney, Agent, or Firm*—Milton L. Honig

[57] ABSTRACT

A cosmetic composition is provided which includes ascorbic acid (Vitamin C) stabilized by dimethyl isosorbide in a pharmaceutically acceptable carrier. Among the preferred carriers are polyols such as polyethylene glycol, propylene glycol and mixtures thereof. Aesthetic properties are improved by the presence of a crosslinked non-emulsifying siloxane elastomer and a volatile siloxane.

7 Claims, No Drawings

VITAMIN C DELIVERY SYSTEM

This application claims the benefit of a U.S. Provisional Application 60/022509 filed Jun. 28, 1996 now abandoned.

BACKGROUND OF THE INVENTION

1. Field of the Invention

The invention relates to a cosmetic product that can stably store ascorbic acid and then deliver same to the skin.

2. The Related Art

Ascorbic acid, also known by its common name of Vitamin C, has long been recognized as an active substance benefiting skin appearance. Vitamin C reportedly increases the production of collagen in human skin tissue. Wrinkles and fine lines are thereby reduced. An overall healthier and younger-looking appearance results. Vitamin C has also found utility as an ultraviolet ray blocking or absorbing agent. Whitening or bleaching skin compositions have also employed Vitamin C utilizing its property of interference with the melanin formation process. There also is a belief that ascorbic acid interacts with the human immune system to reduce sensitivity to skin aggravating chemicals. Reduced levels of Vitamin C concentration on the skin have also been implicated with an increase in stress. From all of the foregoing perspectives, Vitamin C or ascorbic acid may provide significant benefit when topically applied.

Unfortunately, Vitamin C is a very unstable substance. Although it is readily soluble in water, rapid oxidation occurs in aqueous media. Solubility of ascorbic acid has been reported to be relatively poor in nonaqueous media, thereby preventing an anhydrous system from achieving any significant level of active concentration. A system is necessary for dissolving or at least uniformly suspending Vitamin C which is also chemically compatible with the active.

The art has sought to overcome the problem in a variety of ways. One approach is the preparation of ascorbic acid derivatives. These derivatives have greater stability than the parent compound and, through biotransformation or chemical hydrolysis, can at the point of use be converted to the parent acid. For instance, U.S. Pat. No. 5,137,723 (Yamamoto et al) and U.S. Pat. No. 5,078,989 (Ando et al) provide glycosylate and ester derivatives, respectively.

U.S. Pat. No. 4,818,521 (Tamabuchi) describes under the background technology a so-called two-pack type cosmetic wherein Vitamin C powder and other ingredients are separately packaged in different containers with mixing just prior to use of the cosmetic. The mixing procedure and expensive packaging were said to be drawbacks of this system. The patent suggests stable oil-in-water type emulsions that are weakly acidic and wherein ascorbic acid has been premixed with a stabilizing oil.

Maintenance of pH below about 3.5 has also been suggested in U.S. Pat. No. 5,140,043 (Darr et al) as a stabilization means for aqueous compositions of ascorbic acid.

Water compatible alcohols such as propylene glycol, polypropylene glycol and glycerol have been suggested as co-carriers alongside water to improve stability. An illustration of this approach can be found in U.S. Pat. No. 4,983,382 (Wilmott and Znaiden). Therein a blend of water and water-miscible organic solvent are combined as a stabilizing system. At least about 40% of the organic solvent must be ethanol while the remainder may be selected from such alcohols as propylene glycol, glycerin, dipropylene glycol and polypropylene glycol.

Japanese Patent 44-22312 (Shionogi) describes the stabilization of Vitamin C in a mainly aqueous medium by a variety of glycols. These include polyethylene glycol, ethylene glycol, diethylene glycol and even ethanol. These formulations are intended for ingestion.

U.S. Pat. No. 4,372,874 (Modrovich) has reported incorporation of relatively large amounts of ascorbic acid in a polar water-miscible organic solvent such as dimethyl sulfoxide. Levels of water are kept below 0.5% through addition of a particulate desiccant to the carrier. Although highly polar systems such as dimethyl sulfoxide may be effective, this and related carriers are toxicologically questionable.

Accordingly, it is an object of the present invention to provide a delivery system for ascorbic acid in which the compound is soluble or at least uniformly dispersible and oxidatably storage stable.

Another object of the present invention is to provide a delivery system which assists the penetration of ascorbic acid into the human skin while avoiding irritation thereof.

Still another object of the present invention is to provide a system for delivering ascorbic acid that is aesthetically pleasing and imparts a soft and smooth skinfeel.

These and other objects of the present invention will become more readily apparent through the following summary, detailed discussion and Examples.

SUMMARY OF THE INVENTION

A cosmetic composition is provided that includes:
(i) from 0.001 to 50% by weight of ascorbic acid;
(ii) from 0.1 to 20% by weight of dimethyl isosorbide; and
(iii) a pharmaceutically acceptable carrier present in an effective amount to deliver the ascorbic acid to skin.

DETAILED DESCRIPTION OF THE INVENTION

Now it has been discovered that ascorbic acid can be stabilized against decomposition and uniformly dispersed through use of dimethyl isosorbide in a pharmaceutically acceptable carrier. Dimethyl isosorbide is known in Chemical Abstracts as 1,4:3,6 dianhydro-2,5-di-o-methyl-D-glucitol. Commercially it is available from ICI Surfactants under the trademark Arlasolve DMI. Amounts of this material may range from 0.1 to 20%, preferably from 0.5 to 10%, optimally from 1 to 8% by weight.

Ascorbic acid is available from several sources including Roche Chemicals. Amounts of this material may range from 0.001 to 50%, preferably from 0.1 to 10%, optimally from 1 to 10% by weight.

Compositions of this invention will require a pharmaceutically acceptable carrier. Generally the carrier will be an ingredient present in highest amounts in the cosmetic composition. These amounts may range from 10 to 99.9%, preferably from 25 to 90%, optimally from 50 to 85% by weight. Pharmaceutically acceptable carriers may be selected from water, polyols, silicone fluids, esters and mixtures thereof. When present, water may range from 0.5 to 20%, preferably from 1 to 10%, usually from 2 to 6%, optimally less than 5% by weight of the composition.

Advantageously one or more polyols are present as carriers in the compositions of this invention. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof. Most preferably the polyol is a mixture of polyethylene glycol, molecular weight ranging from 200 to 2,000, and propylene glycol. Preferred weight ratios of polyethylene glycol to propylene glycol range from 5:1 to 1:10, preferably from 2:1 to 1:5, optimally 1:1 to 1:2. Amounts of the polyol may range from 1 to 50%, preferably from 10 to 40%, optimally from 25 to 35% by weight of the composition.

Silicone oils may also be included as carriers in the compositions of this invention. These oils may be either volatile or nonvolatile. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Cyclomethicone is the common name of the preferred volatile silicone oil and is available as a tetramer or pentamer. Amounts of the volatile siloxane will range from 10 to 80%, preferably from 20 to 70%, optimally from 30 to 65% by weight of the composition.

Linear volatile silicone materials generally have viscosities less than about 5 centistokes at 25° C. while cyclic materials typically have viscosities of less than about 10 centistokes.

Examples of preferred volatile silicone oils useful herein include: Dow Corning 344, Dow Corning 345 and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The nonvolatile silicone oils useful in compositions of this invention are exemplified by the polyalkyl siloxanes, polyalklyaryl siloxanes and polyether siloxane copolymers. The essentially nonvolatile polyalkyl siloxanes useful herein include, for example, polydimethyl siloxanes with viscosities of from about 5 to about 100,000 centistokes at 25° C. Among the preferred nonvolatile silicones useful in the present compositions are the polydimethyl siloxanes having viscosities from about 10 to about 400 centistokes at 25° C. Such polyalkyl siloxanes include the Viscasil series (sold by General Electric Company) and the Dow Corning 200 series (sold by Dow Corning Corporation). Polyalkylaryl siloxanes include poly(methylphenyl)siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Cetyl dimethicone copolyol and cetyl dimethicone are especially preferred because these materials also function as emulsifiers and emollients. The former material is available from Goldschmidt AG under the trademark Abil EM-90. Amounts of the nonvolatile siloxane may range from 0.1 to 40%, preferably from 0.5 to 25% by weight of the composition.

Esters may also be incorporated into the cosmetic compositions as pharmaceutically acceptable carriers. Amounts may range from 0.1 to 50% by weight of the composition. Among the esters are:

(1) Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. Particularly preferred are $C_{12}$–$C_{15}$ alcohol benzoate esters.

(2) Alkenyl esters of fatty acids having 10 to 20 carbon atoms. Examples thereof include oleyl myristate, oleyl stearate, and oleyl oleate.

(3) Ether-esters such as fatty acid esters of ethoxylated fatty alcohols.

(4) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(5) Wax esters such as beeswax, spermaceti, myristyl myristate, stearyl stearate.

(6) Sterols esters, of which cholesterol fatty acid esters are examples thereof.

Aesthetic properties and stabilization of emulsions incorporating the Vitamin C may be improved through addition of a crosslinked non-emulsifying siloxane elastomer. Average number molecular weight of these elastomers should be in excess of 10,000, preferably in excess of 1 million and optimally will range from 10,000 to 20 million. The term "non-emulsifying" defines a siloxane from which polyoxyalkylene units are absent. Illustrative of the elastomer is a material with the CTFA name of Crosslinked Stearyl Methyl-Dimethyl Siloxane Copolymer, available as Gransil SR-CYC (25–35% active elastomer) from Grant Industries, Inc., Elmwood Park, N.J. Supply of related elastomer may also be available from the General Electric Company.

Amounts of the elastomer may range from 0.1 to 30%, optimally from 1 to 25%, most preferably from 10 to 20% by weight of the composition.

Minor adjunct ingredients may also be included in cosmetic compositions of this invention. These ingredients may be selected from preservatives, fragrances, anti-foam agents, opacifiers, colorants and mixtures thereof, each in their effective amounts to accomplish their respective functions.

The following examples will more fully illustrate the embodiments of this invention. All parts, percentages and proportions referred to herein and in the appended claims are by weight unless otherwise indicated.

EXAMPLE 1

Oxidative stability and uniform dispersion of ascorbic acid by dimethyl isosorbide was evaluated in the experimental and control formulations outlined under Table I. These formulations were examined after two weeks at room temperature and 110° C.

TABLE I

Test Formulations

| COMPONENT | 1A | 1B | 1C | 1D | 1E | 1F |
|---|---|---|---|---|---|---|
| Cyclomethicone | 42.0 | 42.0 | 42.0 | 42.0 | 42.0 | 42.0 |
| Gransil SR CYL | 18.0 | 18.0 | 18.0 | 18.0 | 18.0 | 18.0 |
| Polyethylene Glycol 200 | 20.25 | 23.25 | 25.25 | 28.25 | 29.25 | 30.25 |
| Ascorbic Acid | 5.0 | 5.0 | 5.0 | 5.0 | 5.0 | 5.0 |
| Water | 4.0 | 4.0 | 4.0 | 4.0 | 4.0 | 4.0 |
| Cetyl Dimethicone Copolyol | 0.75 | 0.75 | 0.75 | 0.75 | 0.75 | 0.75 |
| Dimethyl Isosorbide | 10.0 | 7.0 | 5.0 | 2.0 | 0.5 | — |
| Results Ascorbic Acid Retention (%) | | | | | | |
| 2 Weeks at RJ | 97 | 93 | 92 | 83 | 87 | 76 |
| 2 Weeks at 110° C. | 98 | 93 | 91 | 81 | 87 | 77 |

Essentially no degradation of ascorbic acid occurred in the presence of 10% dimethyl isosorbide. See Formulation 1A. Formulations 1B through 1E containing dimethyl isosorbide at levels from 7.0% down to 0.5% exhibited a small amount of ascorbic acid decomposition. Formulation 1F serving as a control establishes that in the absence of dimethyl isosorbide there is a very significant drop in stability.

EXAMPLES 2–5

A series of further examples were prepared. Their compositions are outlined under Table II. These formulations provided good storage stability for the ascorbic acid and were judged to be aesthetically consumer acceptable.

TABLE II

| COMPONENT | 2 | 3 | 4 | 5 |
|---|---|---|---|---|
| Cyclomethicone | 42.0 | 41.6 | 40.0 | 42.0 |
| Gransil SR CYL | 18.0 | 17.9 | 17.3 | 18.0 |
| Propylene Glycol | 16.8 | 14.8 | 15.0 | 15.0 |
| Polyethytene Glycol 200 | 11.0 | 13.7 | 13.5 | 13.5 |
| Ascorbic Acid | 5.0 | 5.0 | 5.0 | 5.0 |
| Dimethyl Isosorbide | 2.0 | 2.0 | 2.0 | 2.0 |
| Cetyl Dimethicone Copolyol | 0.8 | 0.8 | 0.8 | 0.8 |
| Water | balance | balance | balance | balance |

EXAMPLES 6–12

These series of Examples illustrate the scope of the present invention. Various concentrations and different glycol carriers are illustrated.

TABLE III

| COMPONENT | 6 | 7 | 8 | 9 | 10 | 11 | 12 |
|---|---|---|---|---|---|---|---|
| Cyclomethicone | 36.0 | 36.0 | 36.0 | 40.0 | 40.0 | 45.0 | 32.0 |
| Gransil SR CYL | 24.0 | 24.0 | 24.0 | 20.0 | 20.0 | 15.0 | 27.0 |
| Butylene Glycol | 17.5 | — | 17.5 | — | — | — | 29.0 |
| Glycerin | — | 17.5 | — | — | — | — | — |
| Polyethylene Glycol 200 | 10.0 | — | — | 17.5 | 12.0 | 10.0 | 10.0 |
| Polyethylene Glycol 800 | — | 10.0 | 10.0 | 10.0 | 12.0 | 10.0 | — |
| Dimethyl Isosorbide | 2.0 | 2.0 | 2.0 | 4.0 | 5.0 | 10.0 | 1.0 |
| Ascorbic Acid | 1.0 | 1.0 | 1.0 | 4.0 | 4.0 | 5.0 | 0.5 |
| Cetyl Dimethicone Copolyol | 0.8 | 0.8 | 0.8 | 0.8 | 0.8 | — | — |
| Water | bal. | bal. | bal. | bal. | bal. | bal. | bal. |

The foregoing description and Examples illustrate selected embodiments of the present invention and in light thereof variations and modifications will be suggested to one skilled in the art, all of which are within the spirit and purview of this invention.

What is claimed is:

1. A cosmetic composition comprising:

(i) from 0.1 to 10% by weight of ascorbic acid;

(ii) from 0.5 to 10% by weight of dimethyl isosorbide;

(iii) from 0.1% to 30% of a cross linked non-emulsifying siloxane elastomer and (iv) a pharmaceutically acceptable carrier present in an effective amount to deliver the ascorbic acid to skin.

2. The composition according to claim 1 wherein the carrier comprises a polyol in an amount from 1 to 50% by weight of the composition.

3. The composition according to claim 2 wherein the polyol is selected from the group consisting of propylene glycol, dipropylene glycol, polypropylene glycol, polyethylene glycol, sorbitol, hydroxypropyl sorbitol, hexylene glycol, 1,3-butylene glycol, 1,2,6-hexanetriol, glycerin, ethoxylated glycerin, propoxylated glycerin and mixtures thereof.

4. The composition according to claim 2 wherein the polyol is a mixture of polyethylene glycol and propylene glycol in a weight ratio of 2:1 to 1:2.

5. The composition according to claim 1 wherein the carrier comprises water in an amount less than 5% by weight of the composition.

6. The composition according to claim 1 wherein the crosslinked non-emulsifying siloxane elastomer is formed from a divinyl monomer reacting with Si—H linkages of a siloxane backbone.

7. The composition according to claim 1 further comprising from 10 to 80% of a volatile siloxane.

* * * * *